United States Patent
McAlexander

(10) Patent No.: US 10,111,754 B2
(45) Date of Patent: Oct. 30, 2018

(54) ACETABULAR SHELL AND LINER SYSTEM

(71) Applicant: DEPUY SYNTHES PRODUCTS, INC., Raynham, MA (US)

(72) Inventor: Chad Sirvane McAlexander, Fort Wayne, IN (US)

(73) Assignee: DEPUY IRELAND UNLIMITED COMPANY (IE)

( * ) Notice: Subject to any disclaimer, the term of this patent is extended or adjusted under 35 U.S.C. 154(b) by 84 days.

(21) Appl. No.: 15/281,731

(22) Filed: Sep. 30, 2016

(65) Prior Publication Data

US 2018/0092745 A1    Apr. 5, 2018

(51) Int. Cl.
| A61F 2/32 | (2006.01) |
| A61F 2/34 | (2006.01) |
| A61F 2/36 | (2006.01) |
| A61F 2/30 | (2006.01) |

(52) U.S. Cl.
CPC .............. *A61F 2/34* (2013.01); *A61F 2/3609* (2013.01); *A61F 2/3662* (2013.01); *A61F 2002/30616* (2013.01); *A61F 2002/30672* (2013.01); *A61F 2002/3414* (2013.01); *A61F 2002/3448* (2013.01)

(58) Field of Classification Search
CPC .. A61F 2/32; A61F 2/34; A61F 2/4684; A61F 2002/3208; A61F 2002/3448; A61F 2002/3216; A61F 2002/3611; A61F 2250/0064
See application file for complete search history.

(56) References Cited

U.S. PATENT DOCUMENTS

| 3,707,006 | A | 12/1972 | Bokros |
| 5,156,626 | A | 10/1992 | Broderick |
| 5,425,779 | A | 6/1995 | Musler |
| 5,569,263 | A | 10/1996 | Hein |
| 5,865,850 | A | 2/1999 | Matthews |
| 5,888,211 | A | 3/1999 | Sanders |
| 6,284,002 | B1 | 9/2001 | Sotereanos |
| 7,179,297 | B2 | 2/2007 | McLean |
| 7,192,449 | B1 | 3/2007 | McQueen |
| 8,840,676 | B2 * | 9/2014 | Belew ............... A61F 2/4684 623/22.15 |
| 8,858,645 | B2 * | 10/2014 | Grostefon .............. A61F 2/32 623/22.15 |
| 9,724,201 | B2 | 8/2017 | Grostefon |
| 2002/0193882 | A1 | 12/2002 | Koller |

(Continued)

FOREIGN PATENT DOCUMENTS

| CN | 2580920 Y | 10/2003 |
| CN | 101883540 A | 11/2010 |

(Continued)

*Primary Examiner* — Brian Dukert

(57) ABSTRACT

A trial liner system for use in hip arthroplasty. The liner system includes a first trial liner having a generally convex outer surface and a generally concave inner surface, the generally concave inner surface having a first locking mechanism. The liner also includes a second trial liner having a generally convex outer surface and a generally concave inner surface The generally convex outer surface includes a second locking mechanism adapted to lock with the first locking mechanism of the first trial liner when the second trial liner is inserted into the first trial liner.

14 Claims, 5 Drawing Sheets

(56) References Cited

U.S. PATENT DOCUMENTS

| | | |
|---|---|---|
| 2004/0117029 A1 | 6/2004 | Lewis |
| 2004/0199257 A1 | 10/2004 | Dooney |
| 2005/0143828 A1 | 6/2005 | Collins |
| 2007/0250175 A1 | 10/2007 | Meridew |
| 2011/0247229 A1 | 10/2011 | Anapliotis |
| 2012/0185059 A1 | 7/2012 | Vankoski |
| 2012/0319332 A1 | 12/2012 | Mcminn |
| 2013/0204389 A1 | 8/2013 | Kumar |
| 2013/0245775 A1 | 9/2013 | Metcalfe |
| 2013/0325139 A1 | 12/2013 | Steiner |

FOREIGN PATENT DOCUMENTS

| | | |
|---|---|---|
| CN | 102458311 A | 5/2012 |
| DE | 10335442 A1 | 2/2005 |
| DE | 102008030260 A1 | 12/2009 |
| EP | 342014 A1 | 11/1989 |
| EP | 663194 A1 | 7/1995 |
| EP | 0807426 A2 | 11/1997 |
| EP | 1293179 A1 | 3/2003 |
| EP | 1825834 A1 | 8/2007 |
| EP | 2574310 A2 | 4/2013 |
| FR | 1481424 A | 5/1967 |
| FR | 21059985 A5 | 4/1972 |
| GB | 1485295 A | 9/1977 |
| GB | 2152385 A | 8/1985 |
| JP | 4051950 A | 2/1992 |
| JP | 6007386 A | 1/1994 |
| JP | 11155890 A | 6/1999 |
| JP | 2002345858 A | 12/2002 |
| JP | 2003175061 A | 6/2003 |
| JP | 3172112 U | 12/2011 |
| RU | 2309706 C2 | 11/2007 |
| WO | WO 1995022944 A1 | 8/1995 |
| WO | WO 2008117056 A1 | 10/2008 |
| WO | WO 2009106867 A1 | 9/2009 |
| WO | WO 2010129880 A2 | 11/2010 |
| WO | WO 2012035294 A2 | 3/2012 |

\* cited by examiner

ACETABULAR SHELL AND LINER SYSTEM

FIELD OF THE INVENTION

This present invention is directed to a prosthetic shell assembly, and more specifically, a shell system including an acetabular shell and a trial liner system.

BACKGROUND

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the ankle permits a hinge movement, the knee allows for a combination of gliding and hinge movements and the shoulder and hip permit movement through a ball and socket arrangement.

The joints in the body are stressed or can be damaged in a variety of ways. Gradual wear and tear is imposed on the joints through the continuous use of a joint over the years. The joints that permit motion have cartilage positioned between the bones providing lubrication to the motion and also absorbing some of the forces direct for the joint. Over time, the normal use of a joint may wear down the cartilage and bring the moving bones in a direct contact with each other. In contrast, in normal use, a trauma to a joint, such as the delivery of a large force from an automobile accident for example, may cause considerable damage to the bones, the cartilage or to other connective tissue such as tendons or ligaments.

Arthropathy, a term referring to a disease of the joint, is another way in which a joint may become damaged. One form of joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthropathy is osteonecrosis, which is caused by the death of a part of the bone due to loss of blood supply and subsequent degeneration of the cartilage. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted. The hip joint is a ball and socket joint that joins the femur or thighbone with the pelvis. The pelvis has a hemispherical socket called the acetabulum for receiving the head of the femur. Both the head of the femur and the acetabulum are coated with cartilage for allowing the femur to articulate within the pelvis. Other joints commonly afflicted include those of the spine, knee, shoulder, elbow, carpals, metacarpals, and phalanges of the hand. One means to address this affliction is arthroplasty which commonly refers to the making of an artificial joint. In severe cases of arthritis or other forms of arthropathy, such as when pain is overwhelming or when a joint has a limited range of mobility, a partial or total replacement of the joint may be justified. The procedure for replacing the joint varies, of course, with the particular joint in question, but in general involves replacing a terminal portion of an afflicted bone with a prosthetic implant and inserting a member with structural support to serve as a substitute for the cartilage.

The prosthetic implant is formed of a rigid material that becomes bonded with the bone and provides strength and rigidity to the joint and a bearing member chosen to allow for lubrication to the joint. Suitable materials for the implant include metals and composite materials such as titanium, cobalt chromium, stainless steel, ceramic and suitable materials for the bearing include polyethylene, metal and ceramics. A cement may also be used to secure the prosthetic implant to the host bone.

Total hip replacement, for example, involves removing the ball shaped head of the femur and inserting a stemmed implant into the center of the bone, which is referred to as the medullary canal of the bone. The stem implant may be cemented into the medullary canal or may have a porous coated surface for allowing the bone to heal directly to the implant. The stemmed implant has a neck and a ball shaped head, which are intended to perform the same functions as the neck and head of a healthy femur. The acetabulum of the patient is reamed to receive a shell and liner. A polyethylene, metal, or ceramic liner with a metal shell is inserted into the acetabulum and acts as socket for receiving the head on the stemmed implant. In many current shell and liner constructs, the shell has a female taper adapted to engage a portion of the liner.

During surgery, it is often desirable to place a trial shell and liner into the acetabulum to ensure proper sizing. The trial liner then is coupled with a trial head to determine a number of biomechanics factors such as range of motion, joint tension, and leg length. The trial liner could also be coupled with an implanted head to determine these factors. One drawback to present systems is that each liner has a specific inner and outer diameter. The user must select the liner with the appropriate outer and inner diameter for the head. This creates a lot of unnecessary inventory to be brought into the operating room. Furthermore, the trial liners must all be placed separately, taking up room in the instrument case.

SUMMARY

According to one embodiment, a trial liner system for use in hip arthroplasty is provided. The liner system includes a first trial liner having a generally convex outer surface and a generally concave inner surface, the generally concave inner surface having a first locking mechanism. The liner also includes a second trial liner having a generally convex outer surface and a generally concave inner surface The generally convex outer surface includes a second locking mechanism adapted to lock with the first locking mechanism of the first trial liner when the second trial liner is inserted into the first trial liner.

According to another embodiment of the present invention, a trial liner system for use in hip arthroplasty is provided. The system includes a plurality of nesting trial liners. Each one of the plurality of trial liners has an outer diameter and an inner diameter that is a different size than the others of the plurality of trial liners. The outer diameter of at least one of the plurality of trial liners is sized so as to fit within the inner diameter of at least one of the plurality of trial liners.

According to yet another embodiment of the present invention, a hip arthroplasty system is provided. The system includes a plurality of nesting trial liners. Each one of the plurality of trial liners includes an outer diameter and an inner diameter that is a different size than the others of the plurality of trial liners. The outer diameter of at least one of the plurality of trial liners is sized so as to fit within the inner diameter of at least one of the plurality of trial liners. The system also includes a plurality of trial heads. At least one of the plurality of trial heads has a diameter such that it fits within the inner diameter of one of the plurality of nesting trial liners. The system also includes at least one stem including a neck for coupling with the plurality of trial heads.

BRIEF DESCRIPTION OF FIGURES

FIG. 3b illustrates a single nesting liner of a size different than the liner of FIG. 3a.

DETAILED DESCRIPTION

Figure 1:
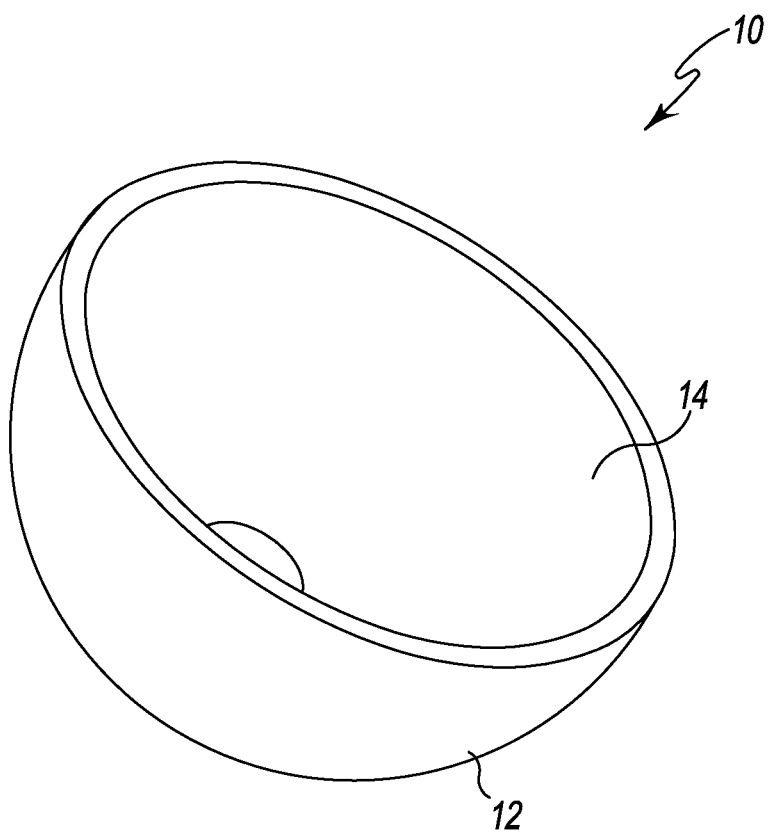
FIG. 1 illustrates a trial shell according to one embodiment of the present invention.

An acetabular trial shell 10 according to one embodiment of the present invention is shown in FIG. 1. As illustrated, the trail shell includes an outer convex surface 12 and an inner concave surface 14. The outer convex surface 12 is to engage the prepared bone of a patient's acetabulum. The inner concave surface 14 is designed to accept a trial liner system 20 as shown in FIG. 2.

Figure 2:
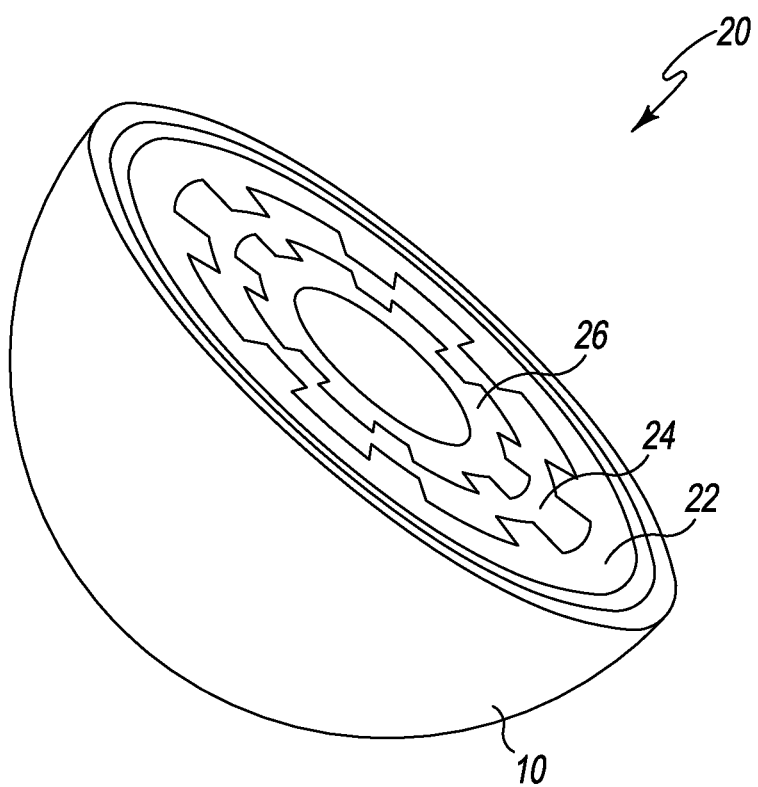
FIG. 2 illustrates a trial nesting liner set inserted into the shell of FIG. 1.

As shown in FIG. 2, the trial liner system 20 includes three trial liners 22, 24, 26 in nesting engagement with each other and with the trial shell 10. The illustrated embodiment shows three trial liners 22, 24, 26 as being the trial liner system 20, but it should be understood that any number of trial liners may be used.

Figure 3A:
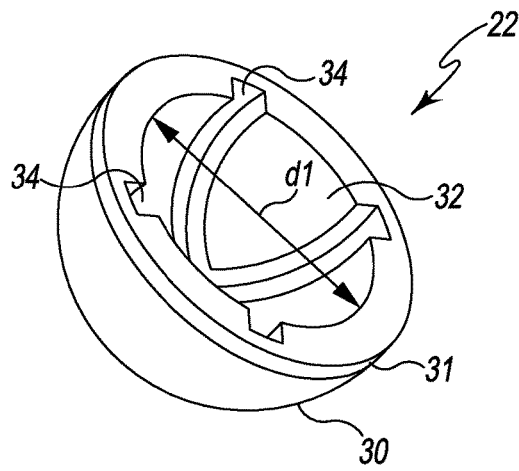
FIG. 3a illustrates a single nesting liner according to one embodiment of the present invention.

Turning now to FIG. 3a, the largest of the illustrated trial liners 22 will be described. The trial liner 22 has a generally convex outer surface 30. The convex outer surface 30 is sized and shaped to engage the inner concave surface 14 of the shell 10. The diameter of the outer surface 30 is approximately the same as the diameter of the inner concave surface 14. The outer surface 30 may also include locking features 31 such as a taper (as shown) or a thread at the center of the cup and liner (not shown). In other embodiments, tapers and locking rings could be used. Alternatively, there may not be a locking feature and the trial could be loose. The trial liner 22 also includes a generally concave inner surface 32. The inner surface 32 is interrupted by a plurality of locking mechanisms 34. In the illustrated embodiment, the locking mechanisms 34 are recesses. Alternatively, the locking mechanisms may be protrusions. The generally concave inner surface 32 has a diameter, d1, which is large enough to receive the largest size head (36 in FIG. 4b) that may be used with the system.

Figure 3B:
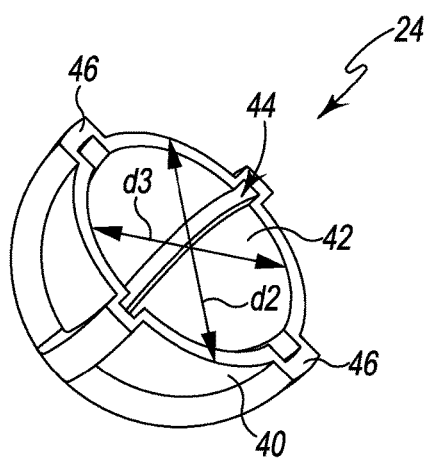

FIG. 3b illustrates the next largest trial liner 24. The trial liner 24 has a generally convex outer surface 40. The diameter d2 of the generally convex outer surface 40 is approximately the same as the diameter d1 of the concave inner surface of the largest trial liner 22. The convex outer surface 40 also includes a locking mechanism 46 sized and shaped to engage the locking mechanism 34 of the largest trial liner 24. As shown, the locking mechanism 46 is a protrusion that engages the recess 34 of the liner trial 22. As shown, there are a plurality of protrusions 46 and corresponding recesses 34. Alternatively, there may be only a single protrusion 46 and corresponding recess 34. In other embodiments, the second liner 24 may include recesses and the first liner 22 may include protrusions. In yet other locking mechanisms such as tapers or tongue-in-groove mechanisms may be utilized.

The trial liner 24 also includes a generally concave inner surface 42. The inner surface 42 is interrupted by a plurality of locking mechanisms 44. In the illustrated embodiment, the locking mechanisms 44 are recesses. Alternatively, the locking mechanisms may be protrusions. The generally concave inner surface 42 has a diameter, d3, which is large enough to receive the second largest size head that may be used with the system.

Figure 3C:
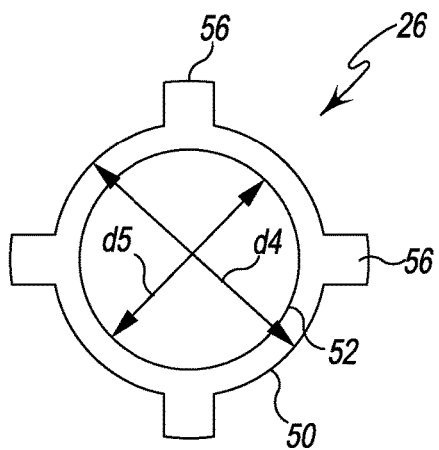
FIG. 3c illustrates a single nesting liner of a size different than both the liners of FIG. 3a and FIG. 3b.

FIG. 3c illustrates the smallest trial liner 26. The trial liner 26 has a generally convex outer surface 50. The diameter d4 of the generally convex outer surface 50 is approximately the same as the diameter d3 of the concave inner surface 42 of the second trial liner 42. The convex outer surface 50 also includes a locking mechanism 56 sized and shaped to engage the locking mechanism 44 of the second trial liner 34. As shown, the locking mechanism 56 is a protrusion that engages the recess 44 of the liner trial 24. As shown, there are a plurality of protrusions 56 and corresponding recesses 44. Alternatively, there may be only a single protrusion 56 and corresponding recess 44. In other embodiments, the third liner 26 may include recesses and the second liner 24 may include protrusions. In yet other locking mechanisms such as tapers or tongue-in-groove mechanisms may be utilized.

The third trial liner 26 also includes a generally concave inner surface 52. In the illustrated embodiment, the inner surface is smooth to receive a head. The inner surface 52 may interrupted by a plurality of locking mechanisms (not shown) which may be recesses or other known locking mechanisms. The generally concave inner surface 52 has a diameter, d5, which is large enough to receive the smallest size head that may be used with the system.

In the system, there may be any number of trial liners with differing sizes of diameters. The invention provides that they are all able to nest. In some embodiments, the locking mechanisms may be ribs that extend all the way around the outer surface of the liner or they may just be tabs at the edges. Also, other known locking mechanisms may be used.

Figure 4A:
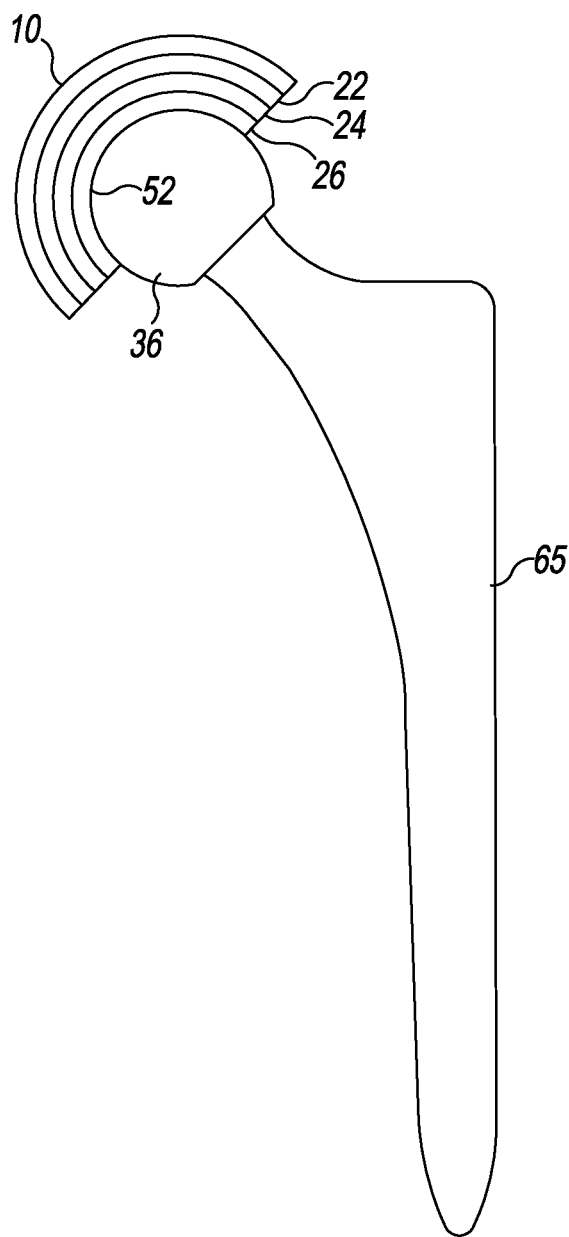
FIG. 4a illustrates a trial nesting liner set inserted into a shell and articulating with a head.

Turning now to FIG. 4a, the system is shown in use with a trial head 36. As shown, the trial shell 10 is coupled to the first trial 22, second trial 24, and third trial 26. The inner surface 52 of the third trial liner 26 is sized and shaped to receive the trail head 36. The trial head 36 is coupled to either a trial stem or a stem implant 65. In other embodiments, the trial head 36 may be coupled to a reamer (not shown) acting as a trail stem.

Figure 4B:
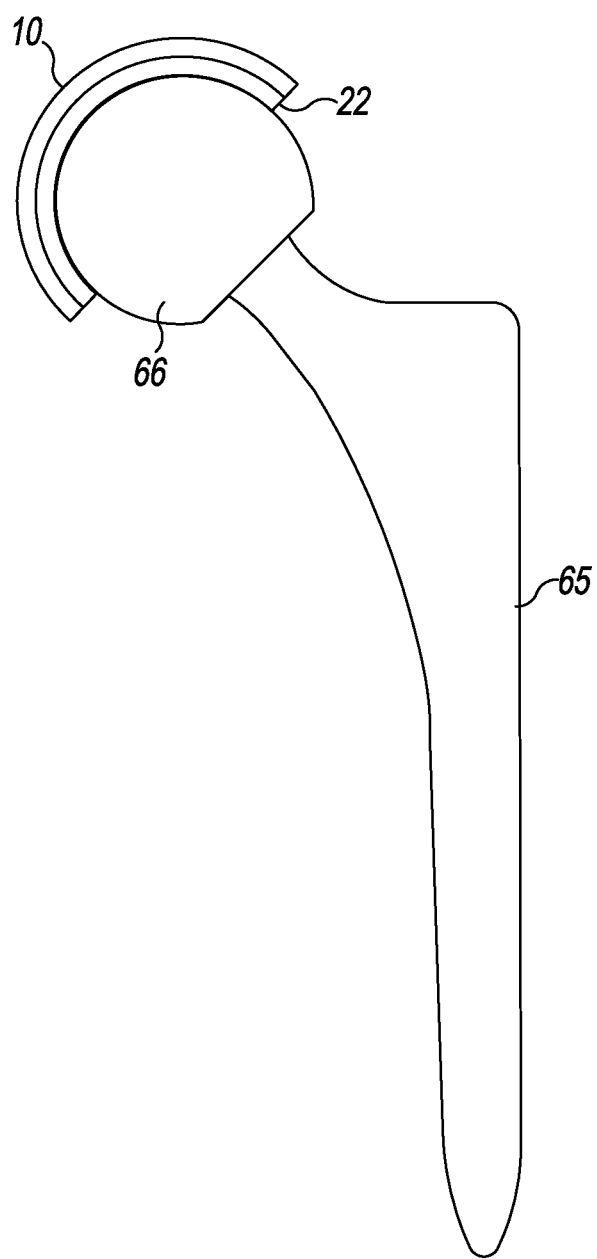
FIG. 4b illustrates a trial nesting liner with the single liner of FIG. 3a inserted into a shell and articulating with a head.

If during the surgery, the surgeon decides to trial a larger head, the surgeon may simply remove the smallest trial liner 26 and insert the next larger trial head into the trial liner 24. Alternatively, as shown in FIG. 4b, the surgeon may start with the largest trial liner 22 and trial the largest head 66 and continue the trialing process by trying successively smaller heads.

The trial shell 10 is made of stainless steel. Alternatively, polymers may be used. The trial liners may be made of durable polymers that are able to be sterilized in an autoclave. Other polymers may be used that are designed to only be used a single time.

In use, any number of nesting trial liners may be used with corresponding size heads. In some embodiments, the trial liners may be used with an actual shell implant and head implants and not trials.

What is claimed is:

1. A trial liner system for use in hip arthroplasty including:
a first trial liner having a generally convex outer surface and a generally concave inner surface, the generally concave inner surface having a first locking mechanism; and
a second trial liner having a generally convex outer surface and a generally concave inner surface, the generally convex outer surface having a second locking mechanism adapted to lock with the first locking mechanism of the first trial liner when the second trial liner is inserted into the first trial liner, wherein one of the first and second locking mechanisms are recesses and the other of the first and second locking mechanisms are protrusions sized and shaped to lock into the recesses and the recess of the first locking mechanism being transverse to the recess of the second locking mechanism such that when the protrusions are locked into the corresponding recesses, the second trial liner cannot move relative to the first trial liner.

2. The trial liner system of claim 1, wherein the first and second recesses are in the inner generally concave surface of the first trail liner and extend across the inner surface.

3. The trial liner system of claim 1, wherein the first and second protrusions are ribs extending across the outer generally convex outer surface of the second trial liner.

4. The trial liner system of claim 1, wherein the second trial liner includes a third locking mechanism on the generally concave inner surface.

5. The trial liner system of claim 4, wherein the third locking mechanism includes a plurality of recesses.

6. The trial liner system of claim 4, further comprising a third trial liner, wherein the trial liner has a generally concave inner surface and a generally convex outer surface, the generally convex outer surface having a plurality of locking mechanisms.

7. The trial liner system of claim 1, wherein the generally concave inner surface of the first and second trial liners are sized and shaped to receive a trial head.

8. A trial liner system for use in hip arthroplasty including:
a plurality of nesting trial liners, with each one of the plurality of trial liners having an outer diameter and an inner diameter that is a different size than the others of the plurality of trial liners, wherein the outer diameter of at least one of the plurality of trial liners is sized so as to fit within the inner diameter of at least one of the plurality of trial liners, each of the plurality of nesting trial liners including a locking mechanism, wherein the locking mechanism of one of the plurality of nesting trial liners includes a first and a second recess and the locking mechanism of another of the plurality of nesting trial liners includes a first and a second protrusion sized and shaped to lock into the recesses and the first recess being transverse to the second recess such that when the first and second protrusions are locked into the first and second recesses, the second trial liner cannot move relative to the first trial liner.

9. The trial liner system of claim 8, wherein the inner diameters of at least one of the plurality of trial liners is sized and shaped to receive a trial head.

10. The trial liner system of claim 8, wherein the inner diameters of each of the plurality of trial liners is sized and shaped to receive a trial head.

11. A hip arthroplasty system including:
a plurality of nesting trial liners, with each one of the plurality of trial liners having an outer diameter and an inner diameter that is a different size than the others of the plurality of trial liners, wherein the outer diameter of at least one of the plurality of trial liners is sized so as to fit within the inner diameter of at least one of the plurality of trial liners;
a plurality of trial heads, at least one of the plurality of trial heads having a diameter such that it fits within the inner diameter of one of the plurality of nesting trial liners;
at least one stem including a neck for coupling with the plurality of trial heads,
wherein the outer diameter of at least one of the plurality of trial liners includes first and second locking mechanisms and the inner diameter of at least another of the plurality of trial liners includes corresponding first and second locking mechanisms, such that when assembled, the first and second locking mechanisms of the outer diameter of one of the plurality of trial liners engage the first and second locking mechanisms of the inner diameter of the another of the plurality of trial liners, the engagement not allowing for the movement of the one of the plurality of trial liners relative to the another of the plurality of trial liners.

12. The hip arthroplasty system of claim 11, wherein the first and second locking mechanism of the outer diameter is one of a groove and a rib, and the first and second locking mechanism of the inner diameter is the other of a groove and a rib.

13. The hip arthroplasty system of claim 11, wherein the inner diameter of third of the plurality of trial liners includes a third locking mechanism, the third locking mechanism adapted to engage the first locking mechanism of the one of the plurality of trial liners.

14. The hip arthroplasty system of claim 11, wherein each of the plurality of liners has a generally convex outer surface and a generally concave inner surface.

* * * * *